United States Patent
Ikadai

(10) Patent No.: US 7,396,352 B2
(45) Date of Patent: Jul. 8, 2008

(54) SKIN CARE DEVICE WITH SUCTION FOR REMOVING IMPURITIES

(75) Inventor: Kazuyasu Ikadai, Osaka (JP)

(73) Assignee: Matsushita Electric Works, Ltd., Osaka (JP)

( * ) Notice: Subject to any disclaimer, the term of this patent is extended or adjusted under 35 U.S.C. 154(b) by 171 days.

(21) Appl. No.: 11/037,254

(22) Filed: Jan. 19, 2005

(65) Prior Publication Data

US 2005/0159684 A1  Jul. 21, 2005

(30) Foreign Application Priority Data

Jan. 19, 2004  (JP) ............................. 2004-011098

(51) Int. Cl.
*A61M 1/00*  (2006.01)
(52) U.S. Cl. ................. 604/540; 604/313; 604/303; 604/315
(58) Field of Classification Search ................. 606/131; 601/6, 17; 604/303, 313, 542–543, 540, 604/315
See application file for complete search history.

(56) References Cited

U.S. PATENT DOCUMENTS

| | | | | |
|---|---|---|---|---|
| 2,710,114 A | * | 6/1955 | Waber et al. ................ 221/232 |
| 4,182,329 A | * | 1/1980 | Smit et al. ..................... 604/23 |
| 5,624,416 A | * | 4/1997 | Schatz ........................ 604/313 |
| 6,319,211 B1 | * | 11/2001 | Ito et al. ......................... 601/7 |

FOREIGN PATENT DOCUMENTS

| | | | |
|---|---|---|---|
| EP | 0251694 A2 | * | 1/1988 |
| EP | 0365230 A2 | * | 10/1989 |
| EP | 0365230 A2 | * | 4/1990 |
| EP | 0997156 | | 5/2000 |
| EP | JP 2001-161438 | * | 6/2001 |
| GB | 2280109 A | * | 1/1995 |
| JP | 53004648 | | 1/1978 |
| JP | 11-196936 | | 7/1999 |
| JP | 2000-197518 | | 7/2000 |
| JP | 2000334009 | | 12/2000 |
| JP | 2001161438 | | 6/2001 |

* cited by examiner

*Primary Examiner*—Tatyana Zalukaeva
(74) *Attorney, Agent, or Firm*—Bacon & Thomas, PLLC

(57) ABSTRACT

A skin care device includes a suction pump for generating a suction force, a suction nozzle detachably attached to a mounting portion of the suction pump and having a first end portion having a suction port with a smaller opening and a second end portion having a suction portion with a larger opening, and a sealing member disposed between an inner peripheral surface of the mounting portion and an outer peripheral surface of the suction nozzle, for sealing a gap between the mounting portion and the suction nozzle. Both of the first end portion and the second end portion are capable of being attached to the mounting portion.

13 Claims, 11 Drawing Sheets

SKIN CARE DEVICE WITH SUCTION FOR REMOVING IMPURITIES

FIELD OF THE INVENTION

The present invention relates to a skin care device for suctioning and removing sebum or cutaneous impurities from the skin (hereinafter, referred to as "skin impurities") by bringing a suction nozzle in contact with the skin; and, more particularly, to a skin care device capable of removing the skin impurities more effectively by allowing a suction port of the suction nozzle to be held more firmly against the areas of and around a user's nose, e.g., the skins around the nostrils or the ridge of the nose.

BACKGROUND OF THE INVENTION

A conventional skin care device is configured to suction and remove skin impurities via a suction nozzle while massaging a suctioned portion of the skin by bringing a suction port of the suction nozzle in contact with the skin and driving a suction pump. However, if the suction port of the suction nozzle is relatively large, it becomes difficult to have the suction port firmly against the areas of the face near the nostrils or the ridge of the nose (hereinafter, referred to as "problematic regions") because of the uneven shape of the region. As a result, gaps would form between the suction port and the skins around or on the nose when the suction port is placed thereon, thereby failing to contact the suction port firmly against the skin, so that the skin impurities cannot be removed sufficiently. Yet, if the size of the suction port of the suction nozzle is made smaller such that the suction port is able to make a firm contact with the problematic regions of the face, there is a downside where the time to treat the entire face would be much longer because the coverage area by the nozzle is also made smaller so that only a small skin area can be treated at once.

Japanese Patent Laid-open Application No. 2000-197518 discloses a skin care device including a suction nozzle with an attachment structure which allows the suction nozzle to be detachably held by the device. However, the technical spirit of this machine resides in the fact that an end portion of the suction nozzle has a dual structure with a larger-diameter annular edge directly contacting the skin and a smaller-diameter buffer edge serving as an actual suction port of the suction nozzle. However, though this skin care device using such a dual structure of the suction nozzle has an effect of preventing a part of the skin from being drawn into the suction nozzle, it is not intended to improve the contacting of the suction nozzle with the problematic regions of the face.

SUMMARY OF THE INVENTION

It is, therefore, an object of the present invention to provide a skin care device capable of being held firmly against any skin areas of user's face including the regions of and around the nostrils or the ridge of the nose, thereby allowing efficient removal of skin impurities from the entire area of and around the nose.

In accordance with a preferred embodiment of the present invention, there is provided a skin care device including: a suction pump for generating a suction force; a suction nozzle detachably attached to a mounting portion of the suction pump and including a first end portion having a suction port with a smaller opening and a second end portion having a suction portion with a larger opening, wherein both of the first end portion and the second end portion are capable of being attached to the mounting portion; and a sealing member disposed between an inner peripheral surface of the mounting portion and an outer peripheral surface of the suction nozzle, for sealing a gap between the mounting portion and the suction nozzle.

BRIEF DESCRIPTION OF THE DRAWINGS

The above and other objects and features of the present invention will become apparent from the following description of a preferred embodiment given in conjunction with the accompanying drawings, in which:

FIG. 4A depicts a perspective view of a suction nozzle viewed from a first end portion having a smaller suction port while

FIGS. 5A and 5B show a modification of the preferred embodiment of the present invention, wherein FIG. 5A illustrates a state when a first end portion with a smaller suction nozzle is used while FIG. 5B shows a state when a second end portion with a larger suction nozzle is used;

DETAILED DESCRIPTION OF THE PREFERRED EMBODIMENTS

Figure 1:
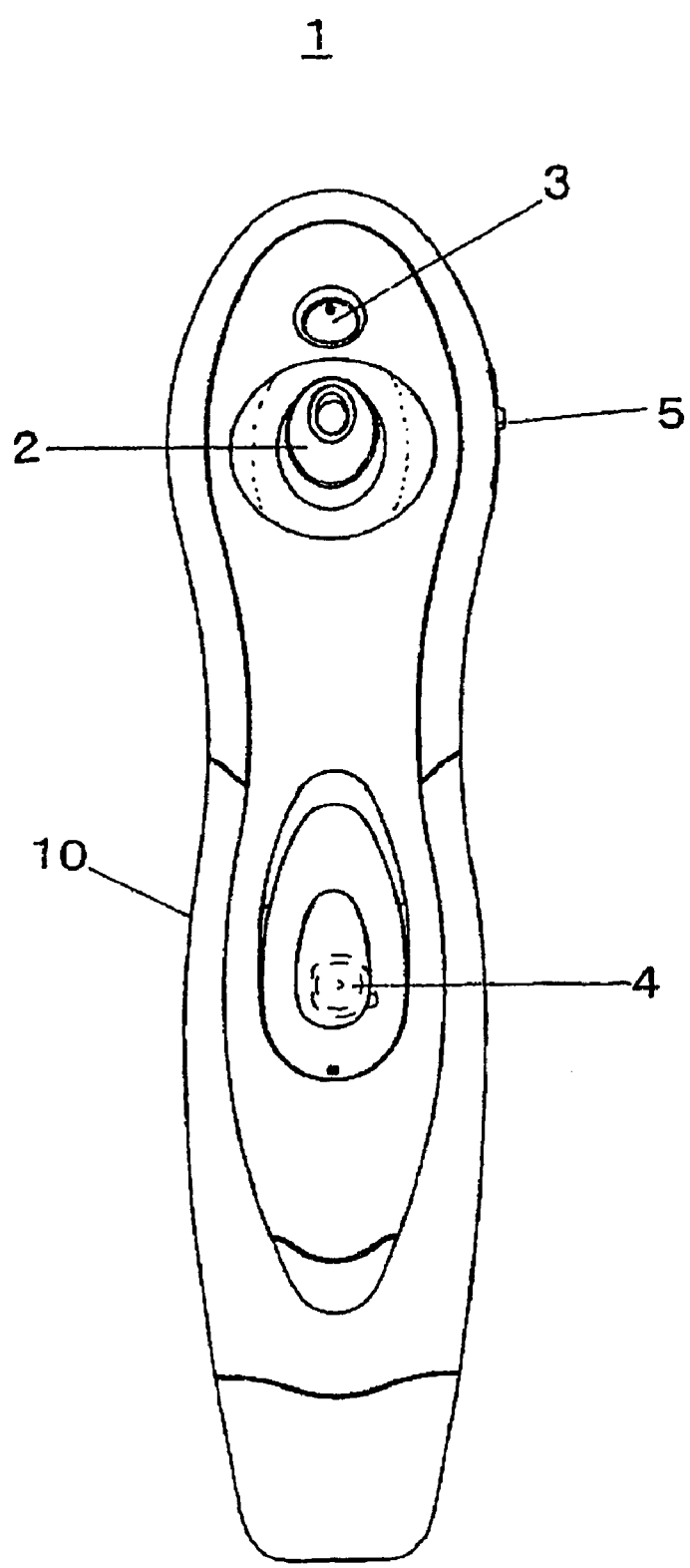
FIG. 1 is a front view of an appearance of a skin care device in accordance with a preferred embodiment of the present invention.

A preferred embodiment of the present invention will be described hereinafter with reference to the accompanying drawings. FIG. 1 is a front view of an appearance of a skin care device 1 in accordance with the preferred embodiment of the present invention and FIG. 2 is a side sectional view showing the internal configuration thereof.

As shown in FIG. 1, an approximately lower half of a housing 10 of the skin care device 1 is a grip portion for allowing a user to hold the device 1. Further, a suction nozzle 2 is installed at an approximately central portion of the upper half of the housing 10 and a mist nozzle 3 for spraying a mist of a liquid toward skin is provided at a position near and above the suction nozzle 2. A main switch 4 for turning on and off the skin care device 1's suctioning operation for suctioning skin impurities is installed at an about central region of a front surface of the housing 10. Further, a mist control switch 5 for turning on and off the liquid ejecting operation is provided at an upper right lateral surface of the housing 10.

Figure 2:
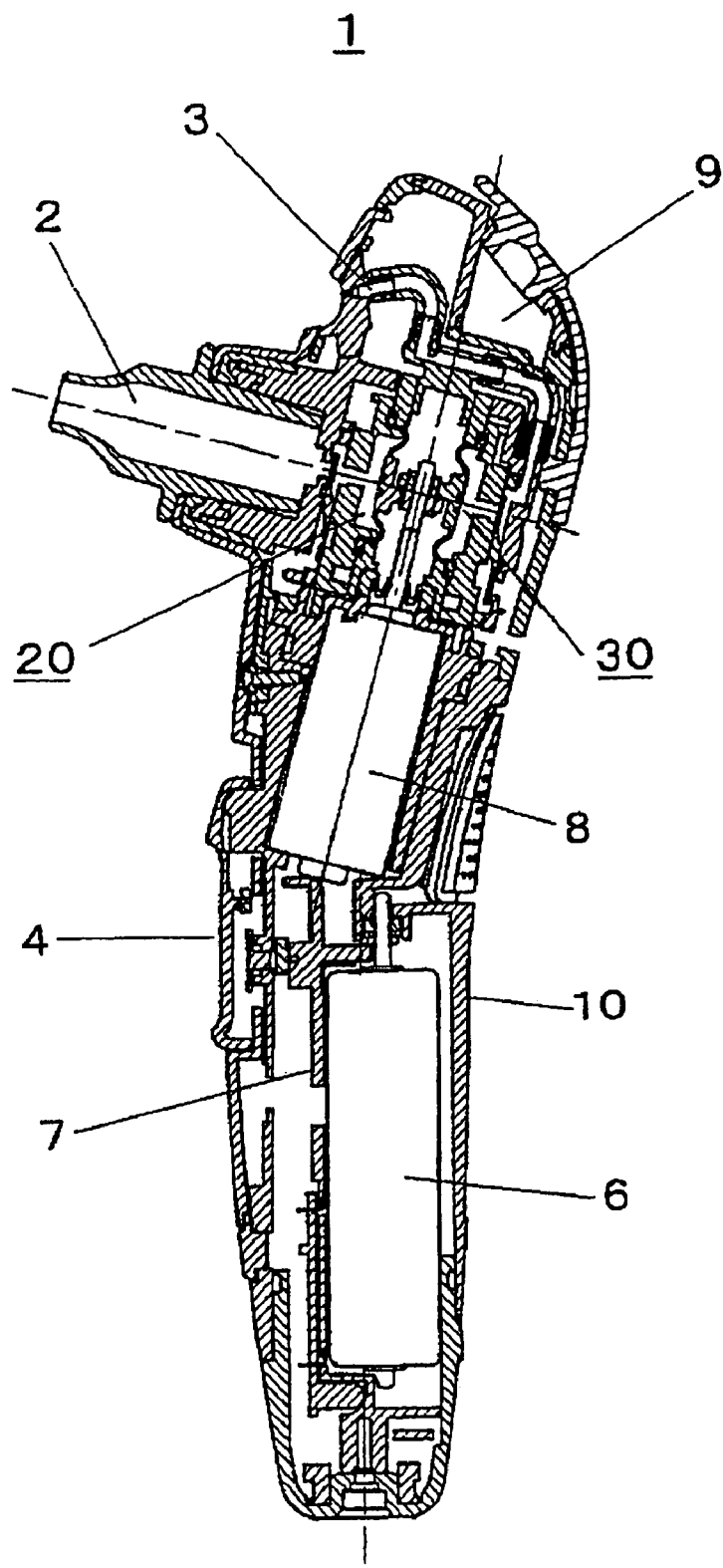
FIG. 2 provides a side sectional view showing an internal configuration of the skin care device.

As can be seen from FIG. 2, incorporated in the grip portion of the housing 10 are a battery 6 such as a rechargeable secondary battery, which serves a power supply of the skin care device 1, a contact terminal 7 of the main switch 4, and so forth. Further, a drive motor 8 is installed at an approximately central portion inside the housing 10, and both a suction pump 20 and a liquid supply pump 30 are disposed above the drive motor 8 and behind the suction nozzle 2, when viewed from the front, to face each other with a rotating shaft 81 interposed therebetween. Further, a liquid storage tank 9 for storing therein a liquid such as water is disposed above the liquid supply pump 30.

The skin care device 1 in accordance with the preferred embodiment of the present invention is configured to drive the suction pump 20 and the liquid supply pump 30 simultaneously by using the single drive motor 8. As a result, the suctioning of skin impurities by the suction nozzle 2 and spraying of liquid by the mist nozzle 3 can be performed at the same time. Moreover, with the employment of the configuration for driving the two pumps 20 and 30 by means of the single drive motor 8, the housing 10 can be reduced in its size with an improved weight balance while making easier to maneuver the skin care device 1.

Figure 3:
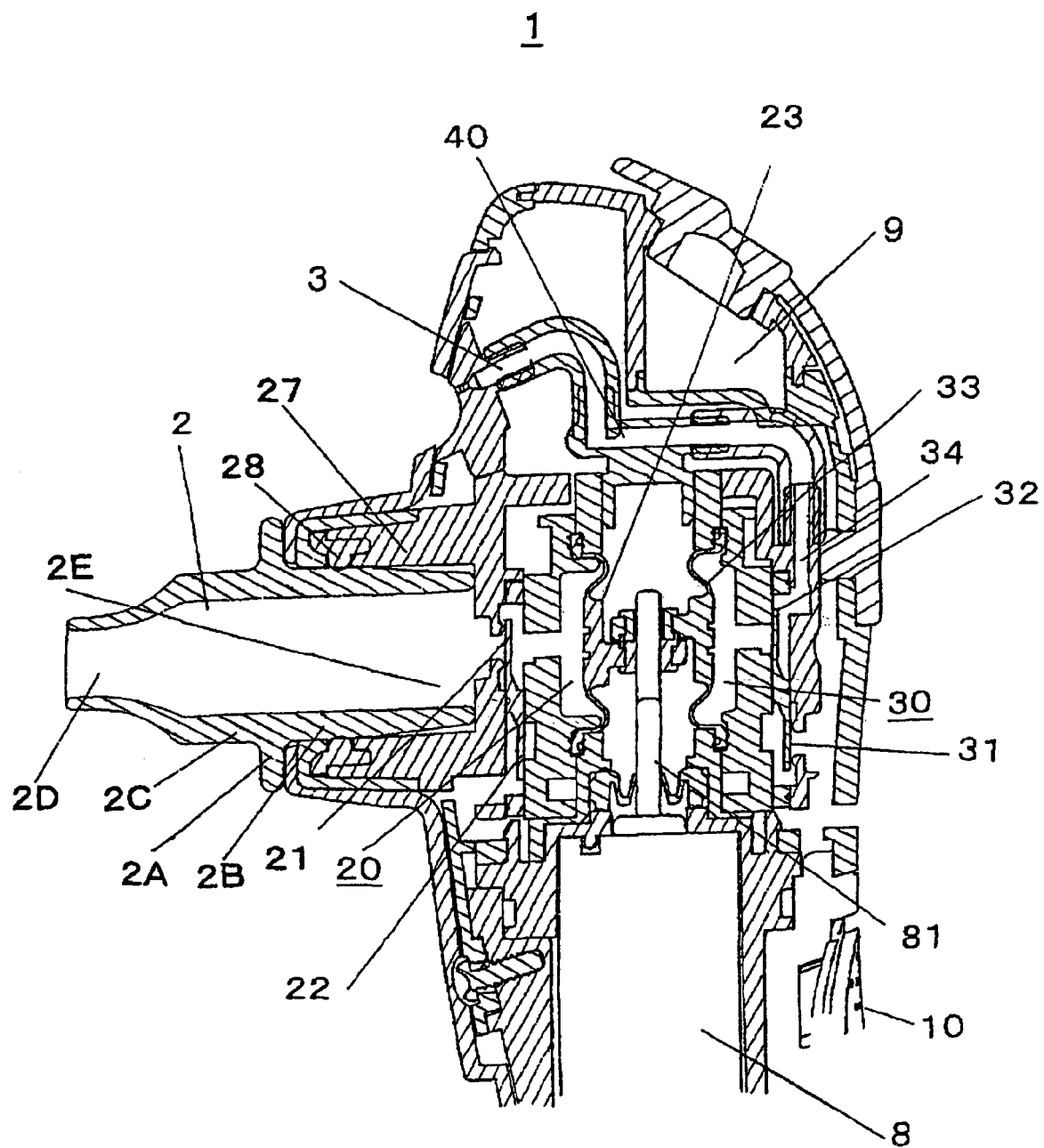
FIG. 3 sets forth an enlarged cross sectional view of parts located above a drive motor shown in FIG. 2.

Referring to FIG. 3, there is provided an enlarged cross sectional view of parts of the skin care device 1 located above the drive motor 8 shown in FIG. 2. The suction pump 20 includes a suction valve 21 for opening or closing a rear end of the suction nozzle 2; an exhaust valve 22 formed as one body with the suction valve 21 to perform on-off operations reverse to those of the suction valve 21; an elastic body (diaphragm) 23 to be deformed to change the volume of the inner space of the suction pump 20; and so forth.

If the elastic body 23 is deformed in a direction that increases the volume of the inner space of the suction pump 20 while a suction port at a front end of the suction nozzle 2 is opened, the suction valve 21 is opened while closing the exhaust valve 22 to thereby take in air from the suction port of the suction nozzle 2. On the contrary, if the elastic body 23 is deformed in a direction that reduces the volume of the inner space of the suction pump 20, the suction valve 21 is closed while opening the exhaust valve 22, so that the air inside the suction pump 20 is discharged from an air outlet.

On the other hand, if the elastic body 23 is deformed in the direction that increases the volume of the inner space of the suction pump 20 while the suction port at the front end of the suction nozzle 2 is in contact with the skin, the suction valve 21 is opened while closing the exhaust valve 22, so that the inner spaces of the suction nozzle 2 and the suction pump 20 are communicated with each other, while increasing the volume. As a result, the internal pressures of the suction nozzle 2 and the suction pump 20 are reduced. Then, if the elastic body 23 is deformed in the opposite direction and reduces the volume of the inner space of the suction pump 20, the suction valve 21 is closed, so that the inner space of the suction nozzle 2 is closed as well while maintaining the internal pressure of the suction nozzle 2. Meanwhile, if the exhaust valve 22 is opened, the air inside the suction pump 20 is discharged through the air outlet, so that the internal pressure of the suction pump 20 is made equal to that of the exterior air. If such alternate deformations of the elastic body 23 are repeated, the internal pressure of the suction nozzle 2 is reduced gradually, generating a suction force. As a result, skin impurities can be taken out from the skin.

Similarly, the liquid supply pump 30 also includes a suction valve 31 communicating with the outside of the liquid supply pump 30 to suction the exterior air; an exhaust valve 32 formed as one body with the suction valve 31 to perform on-off operations reverse to those of the suction valve 31; an elastic body 33 to be deformed to change the volume of the inner space of the liquid supply pump 30; and so forth. An exhaust port 34 of the liquid supply pump 30 is connected to an ejection port of the mist nozzle 3 for ejecting a mist of liquid, to thereby send the air suctioned by the suction valve 31 to the mist nozzle 3 via a connection pipe 40. The mist nozzle 3 generates a mist of liquid from the Venturi effect.

The suction nozzle 2 is configured as an attachment capable of being detachably fitted to the suction pump 20. Specifically, the suction nozzle 2 has a flange 2A formed at an outer periphery of a central portion thereof, and neighboring portions 2B and 2C of the flange 2A have a same outer diameter. The suction nozzle 2 can be detachably connected to a mounting portion 27 of the suction pump 20 and, at this time, its front and rear can be reversed. Further, the opening of a first suction port at a first end portion 2D of the suction nozzle 2 is designed to have a smaller diameter than that of the opening of a second suction port at a second end portion 2E of the suction nozzle 2. Furthermore, the outer diameters of adjacent portions of the first and the second end portion 2D and 2E are set to be smaller than the outer diameters of the neighboring portions 2B and 2C of the flange 2A, respectively. Moreover, in order to prevent air leakage between the suction nozzle 2 and the mounting portion 27 of the suction pump 20, a sealing member 28 formed of, e.g., a resilient material such as rubber is installed such that it is firmly attached to the outer peripheral surface of the suction nozzle 2 and the inner peripheral surface of the mounting portion 27 when the suction nozzle 2 is fitted to the mounting portion 27.

The opening of the first suction port at the first end portion 2D of the suction nozzle 2 is sized so that it ensures tight sealing or cause minimally a gap between the suction port and the skin when it is brought contacts with uneven skins on or around the nostrils or the ridge of the nose. Meanwhile, the opening of the second suction port at the second end portion 2E of the suction nozzle 2 is sized and shaped so that it allows for an efficient suctioning of skin impurities from the face regions other than the nose, e.g., the cheek. Thus, the user can remove skin impurities from a desired treatment area of the face efficiently in a short period of time by changing the mounting direction of the suction nozzle 2 appropriately depending on the area of the face to be treated. Furthermore, it is also possible to suction skin impurities by making the mounting portion 27 contact the skin directly after separating the suction nozzle 2 from the mounting portion 27 of the suction pump 20. In such a case, since the opening of the mounting portion 27 is larger than the opening of the second suction port at the second end portion 2E of the suction nozzle 2, it becomes possible to treat a larger area of the face at one time.

The detailed description of the configuration of FIG. 3 is disclosed in copending, commonly assigned application, U.S. Ser. No. 11/037,075, entitled "SKIN CARE DEVICE".

Figure 4A:
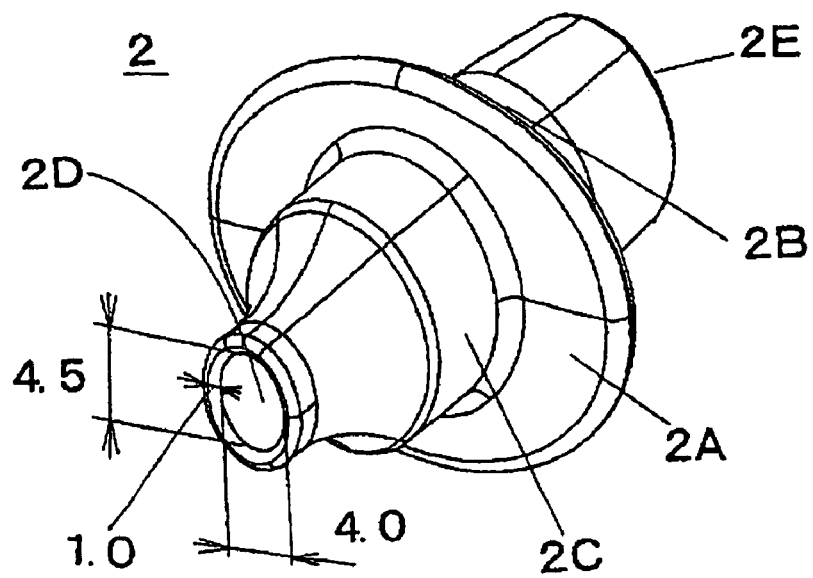
Figure 4B:
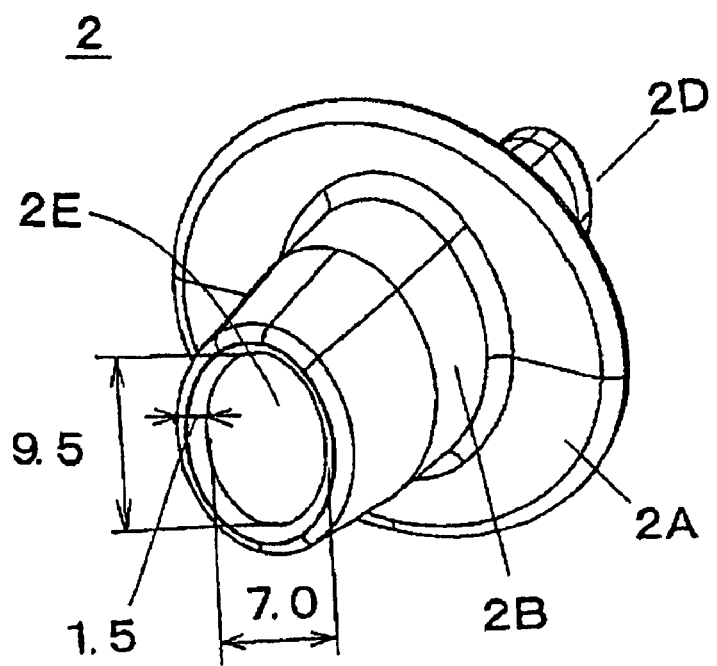
FIG. 4B shows a perspective view of the suction nozzle viewed from a second end portion having a larger suction port.

FIGS. 4A and 4B provide specific dimensions of the suction nozzle 2. FIG. 4A shows the first suction port at the first end portion 2D of the suction nozzle 2 while FIG. 4B shows the second suction port at the second end portion 2E of the suction nozzle 2. As shown in FIG. 4A, the opening of the first suction port at the first end portion 2D has, for example, an approximately elliptical shape with a longer diameter of about 4.5 mm and a shorter diameter of about 4.0 mm. Further, the thickness of a resin formed along the circumference of the first suction port's opening is about 1.0 mm. Referring to FIG. 4B, the opening of the second suction port of the second end portion 2E has, for example, an approximately elliptical shape with a longer diameter of about 9.5 mm and a shorter diameter of about 7.0 mm. Further, the thickness of a resin formed along the circumference of the second suction port's opening is about 1.5 mm. Though the material for the suction nozzle 2 is not limited to any specific one, it is preferable to form the suction nozzle 2 with a resilient material such as hard rubber in order to establish a firmer contact between the suction ports of the suction nozzle 2 and the skin.

As described above, the skin care device 1 in accordance with the preferred embodiment of the present invention is configured to remove the user's skin of skin impurities via the suction nozzle 2 while concurrently spraying liquid from the mist nozzle 3 toward the skin. At this time, in order to efficiently supply the mist of liquid from the mist nozzle 3 to the vicinities of a face portion in contact with the suction nozzle 2, it is preferable to arrange the suction nozzle 2 such that the openings of the first and the second suction ports are extended in a direction connecting the suction nozzle 2 and the mist nozzle 3, that is, a direction of the longer diameter (major axis) of the approximately elliptical shapes of the suction ports extends toward the mist nozzle 3.

Further, it should be noted that the above-specified dimensions are just examples obtained from experiments conducted by the applicants, thus the present invention is not limited thereto. Moreover, the openings of the first and the second suction ports need not be of the approximate elliptical shapes but can have any shapes, e.g., approximately circular shapes. Further, it is apparent that there is no design limitation to the shapes of the openings of the suction ports in case the skin care device does not have the function of spraying a mist.

Figure 5A:
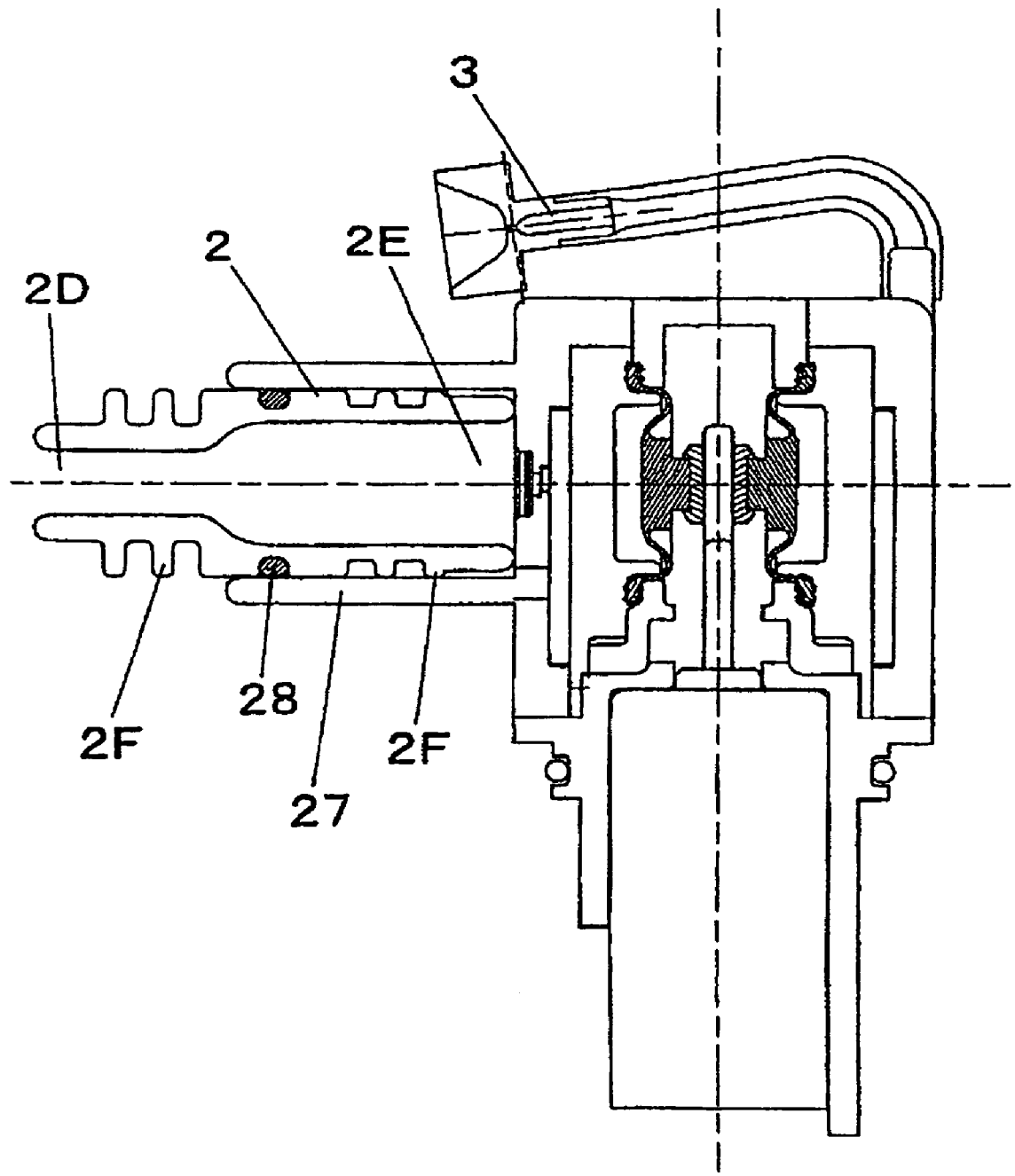
Figure 5B:
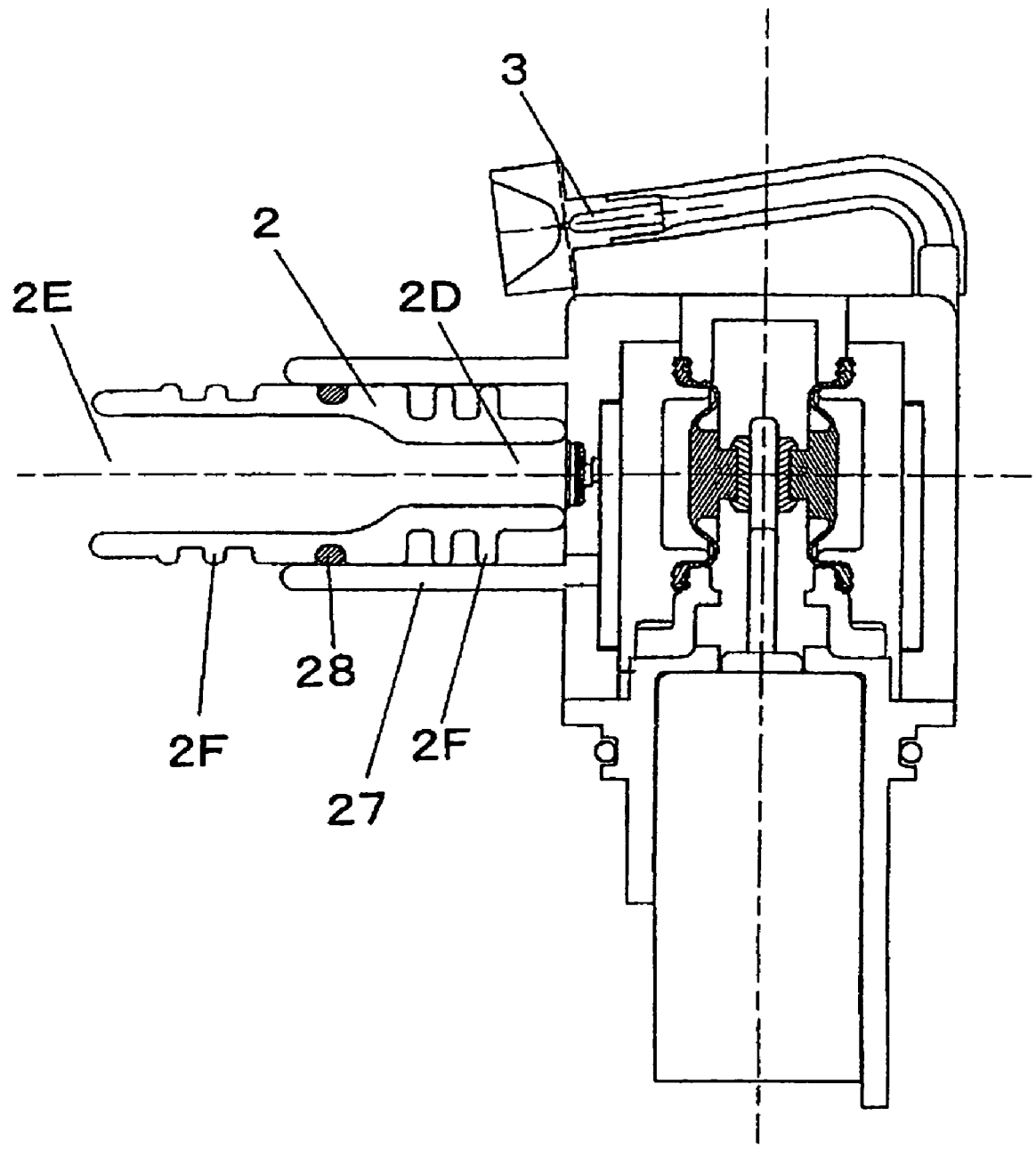

Hereinafter, modifications of the skin care device 1 in accordance with the preferred embodiment of the present invention will be described. In a modification shown in FIGS. 5A and 5B, a suction nozzle 2 is not provided with a flange but a sealing member 28 is installed at an approximately central area of the outer peripheral portion of the suction nozzle 2 with respect to an axial direction thereof. FIG. 5A shows a state where the suction nozzle 2 is coupled to the mounting portion 27 of the suction pump 20 such that a first end portion 2D having a suction port with a smaller-sized opening is oriented outward. FIG. 5B shows a state where the suction nozzle 2 is secured to the mounting portion 27 of the suction pump 20 such that a second end portion 2E having a larger suction port is oriented outward. Annular protrusions 2F each having an outer diameter identical to the inner diameter of the mounting portion 27 are provided at outer peripheral portions of the suction nozzle 2 in order to prevent the suction nozzle 2 from being inclined when it is attached to the mounting portion 27 of the suction pump 20. The protrusions 2F also serve as anti-slipping members for preventing the suction nozzle 2 from slipping when it is connected to or separated from the mounting portion 27. By configuring the suction nozzle 2 to have the sealing member 28 instead of the flange, the same effect as obtained with the formation of the flange can be attained and, further, the outer diameters of the suction nozzle 2 and the mounting portion 27 of the suction pump 20 can be reduced. Referring back to FIG. 3, if the sealing member 28 is installed at the inner peripheral portion of the mounting portion 27 of the suction pump 20, on the other hand, the probability that a user would inadvertently touch the sealing member 28 can be reduced and a damage of the sealing member 28 and a leakage of air due to an attachment error of the sealing member 28 can be prevented though such a configuration has a downside where the outer diameters of the suction nozzle 2 and the suction pump 20 are increased.

Figure 6A:
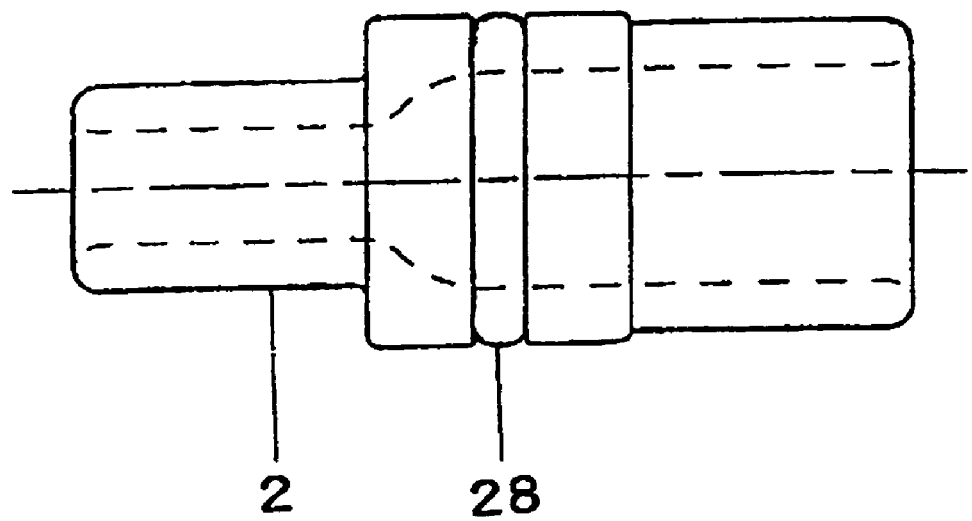
FIGS. 6A and 6B offer side views of modifications of the suction nozzle in accordance with the first embodiment.
Figure 6B:
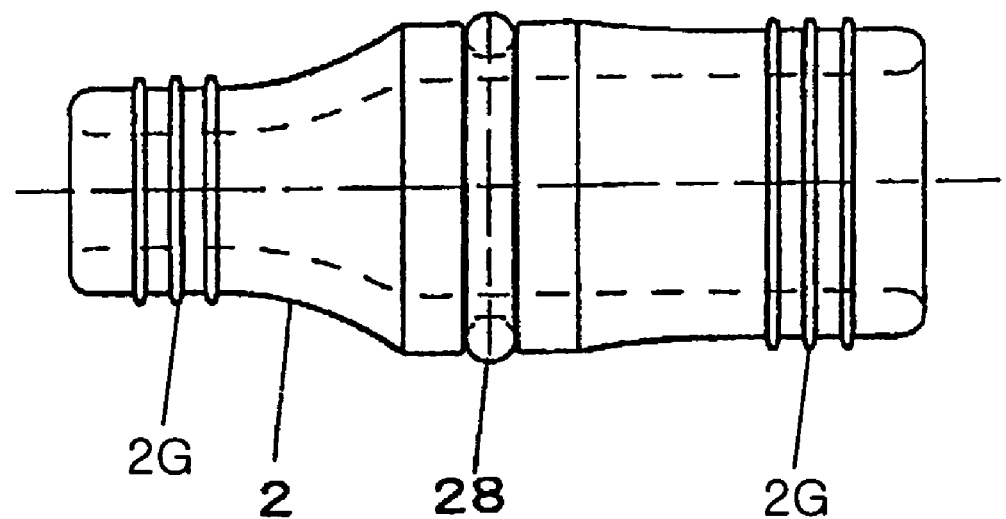

Each of FIGS. 6A and 6B shows another modification of the preferred embodiment of the present invention, in which a sealing member 28 is installed at an approximately central area of the outer peripheral portion of a suction nozzle 2 with respect to the axial direction thereof, as in FIGS. 5A and 5B. FIG. 6A illustrates a suction nozzle 2 whose outer peripheral surface is of a cylindrical shape while FIG. 6B shows a suction nozzle 2 provided with anti-slipping members 2G at outer peripheral surfaces thereof. In comparison with the shape shown in FIGS. 5A and 5B, though the suction nozzles 2 in FIGS. 6A and 6B tend to be inclined more easily when they are attached to the mounting portion 27 of the suction pump 20, they are advantageous in that they have simpler structures and can be formed by using simple molds with an effect of reducing costs for the fabrication thereof.

Figure 7:
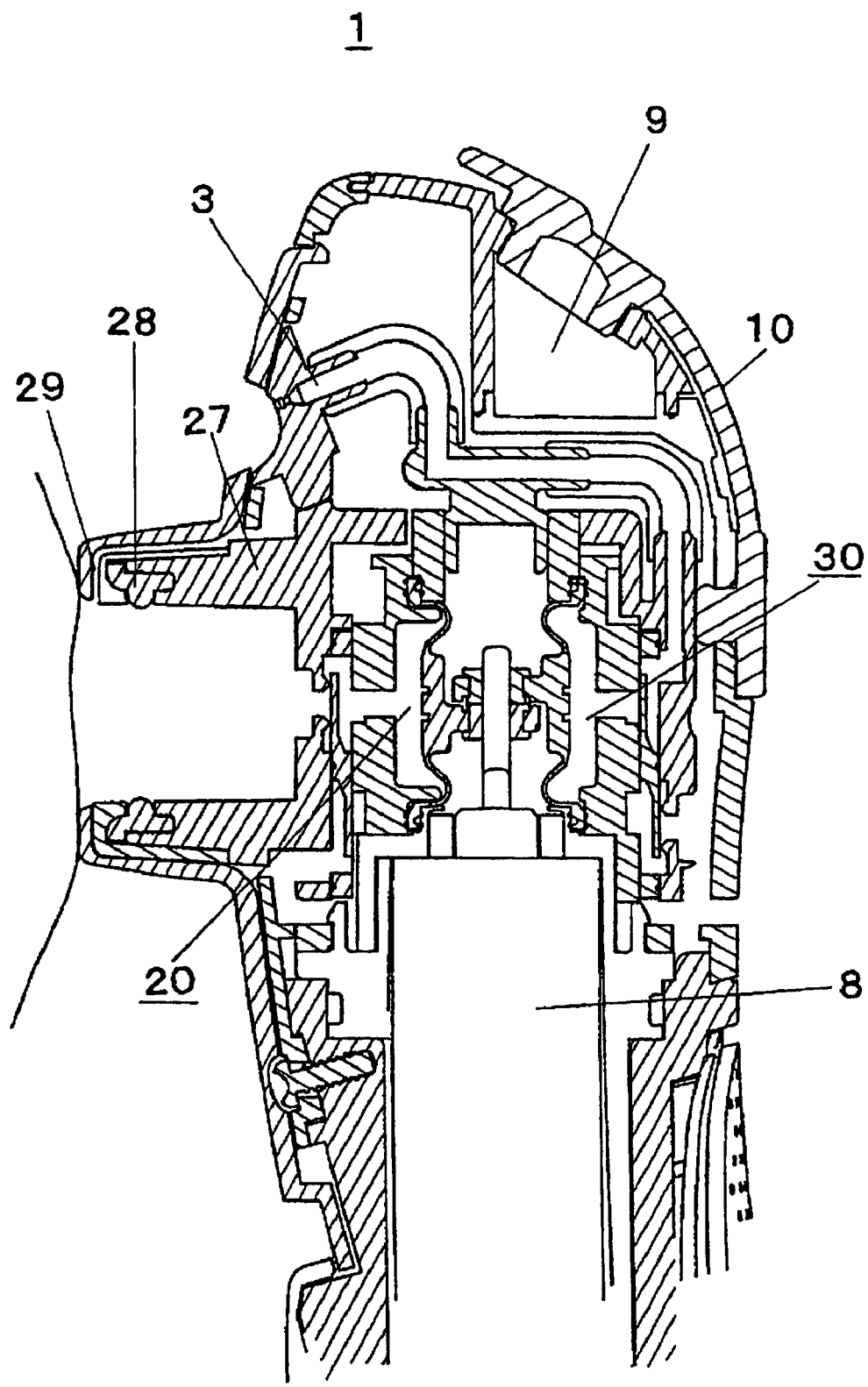
FIG. 7 is a cross sectional side view of another modification of the skin care device of the preferred embodiment of the present invention, wherein the its suction nozzle is removed.
Figure 8:
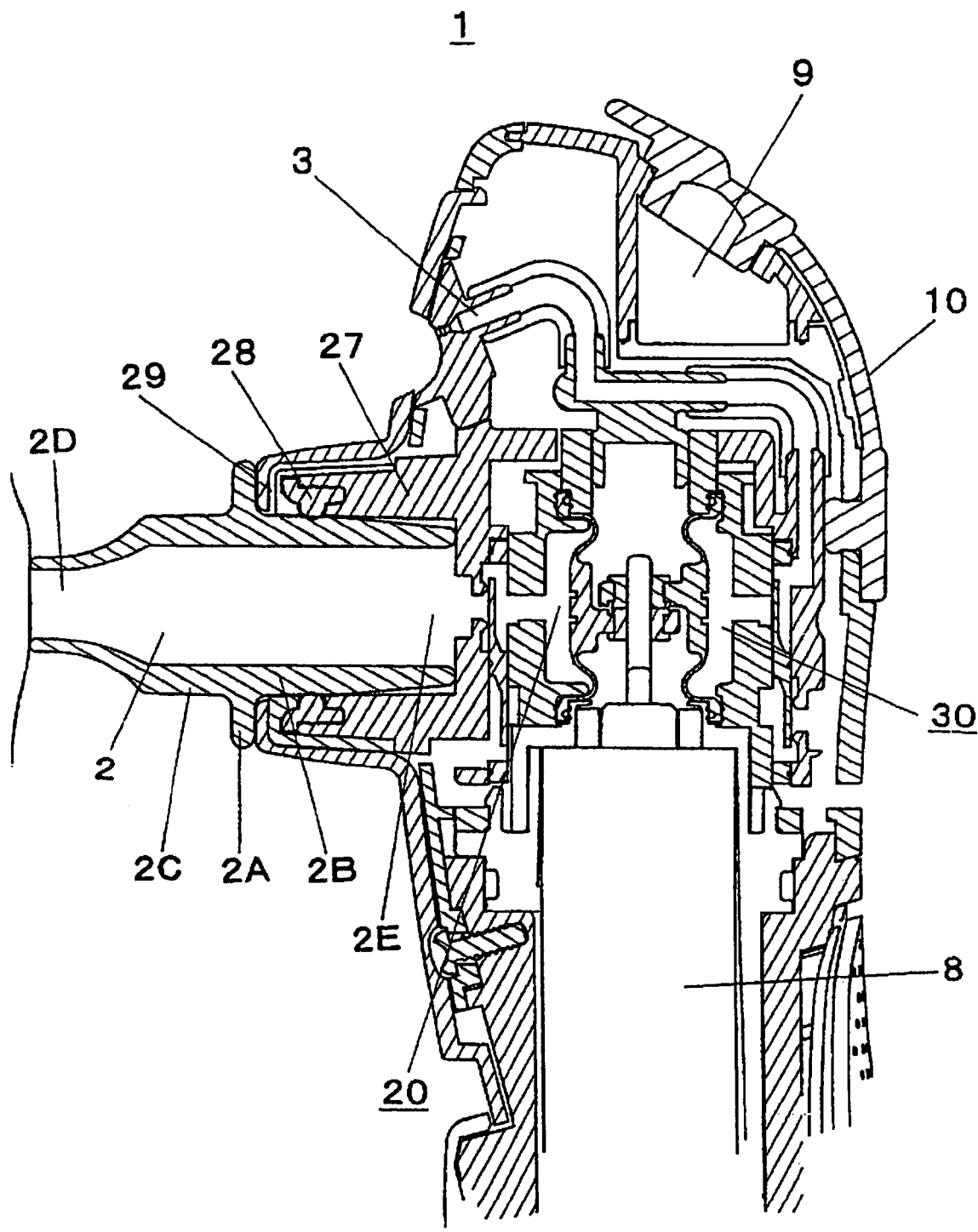
FIG. 8 illustrates a state of using the skin care device shown in FIG. 7 with a suction nozzle fitted in place.

As described before, it is also possible to bring the mounting portion 27 of the suction pump 20 into a direct contact with the skin after separating the suction nozzle 2 from the mounting portion 27. In such a case, there is a likelihood that the skin is drawn into the inside of the mounting portion 27, causing hickey marks due to blood congestion because a suction force is determined by a multiplication of the pressure (negative pressure) of the suction pump 20 and the opening area of a suction port. Thus, it is preferable to provide an elongated hole 29 at one or more locations of the inner peripheral surface of the mounting portion 27 of the suction pump 20, as shown in FIG. 7. By providing the elongated hole 29, the exterior air can be introduced via the elongated hole 29 when the suction nozzle 2 is not coupled, so that the suction force can be appropriately reduced and the problem of the skin being drawn into the inside of the mounting portion 27 can be prevented. As a result, the chance of the user getting hickey marks due to blood congestion can be reduced. Moreover, if the suction nozzle 2 is attached to the mounting portion 27 of the suction pump 20, the elongated hole 29 is closed by the outer peripheral portion of the suction nozzle 2, as shown in FIG. 8, so that skin impurities can be extracted from the skin through the suction ports of the suction nozzle 2 without reducing the suction force.

Figure 9:
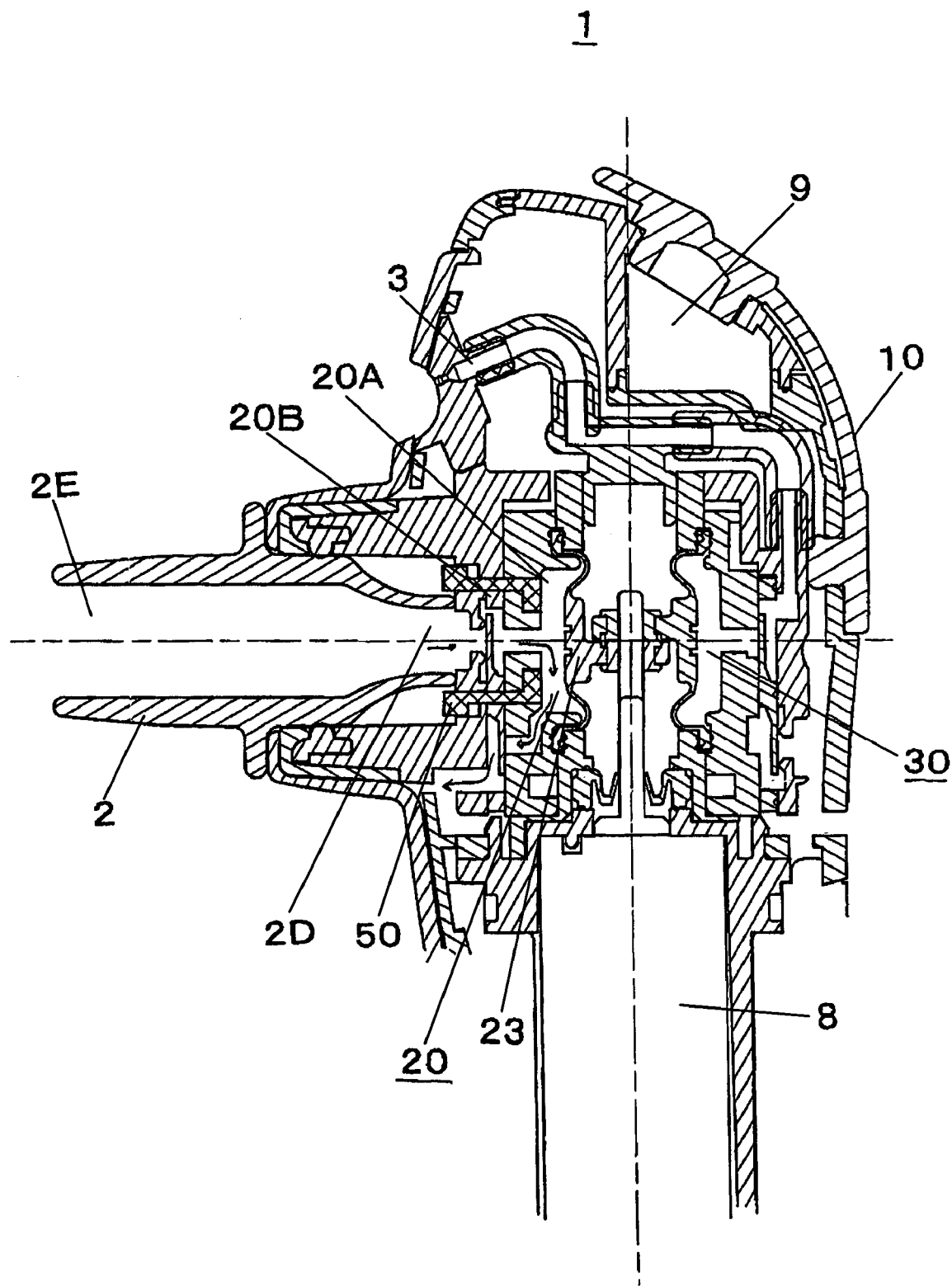
FIG. 9 provides a side sectional view of still another modification of the skin care device in accordance with the preferred embodiment of the present invention, wherein a second end portion with a larger suction nozzle is used.
Figure 10:
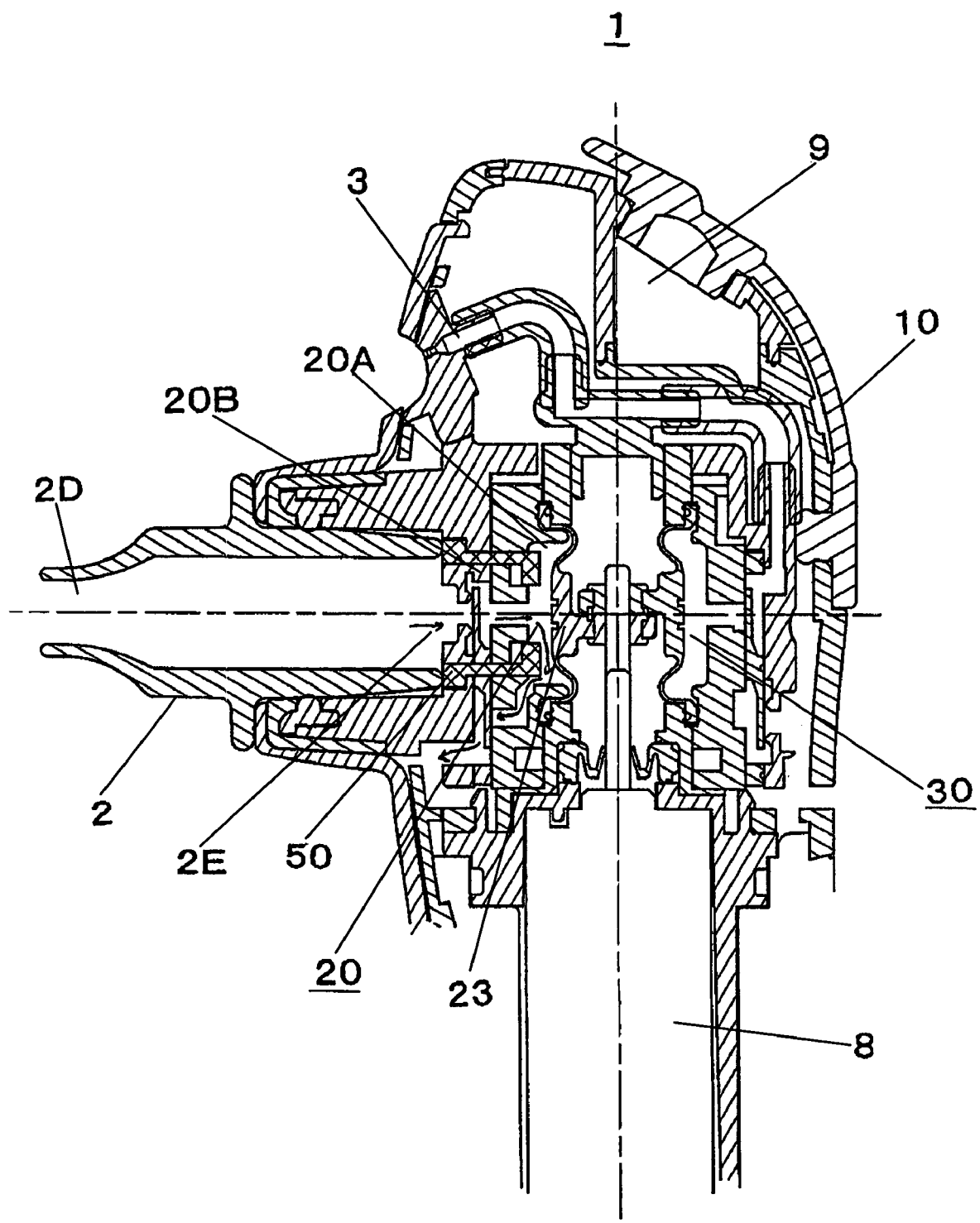
FIG. 10 describes the state of using a first end portion with a smaller suction nozzle in the modification shown in FIG. 9.

Furthermore, the suction force is determined by the multiplication of the pressure of the suction pump 20 and the opening area of a suction port, as described above. Thus, there is a likelihood that a sufficient suction force may not be obtained when a suctioning operation is performed by using a first end portion 2D having a suction port with a smaller opening in case the pressure of the suction pump 20 is set to be at a level capable of producing an optimum suction force when the suctioning operation is performed by using a second end portion 2E having a suction port with a larger opening. In a modification provided in FIGS. 9 and 10, a suction pump 20 is provided with an inner volume control member 50. The inner volume control member 50 is slidably supported at a housing 20B of the suction pump 20 such that it can be projected into an inner space 20A of the suction pump 20. As shown in FIG. 9, in case a suctioning operation is performed by using a second end portion 2E of a suction nozzle 2 where a suction port with a larger opening is located, a first end portion 2D having a suction port with a smaller opening becomes to contact the housing 20B. At this time, the inner volume control member 50 is located at the left in the drawing. Thus, the volume of the inner space of the suction pump 20 is not reduced, thereby making it possible to generate an optimum suction force that can be obtained when the suctioning operation is performed with the second end portion 2E having the larger opening. Meanwhile, if a suctioning treatment is performed by using the first end portion 2D of the suction nozzle 2 where the suction port with the smaller opening is located, the second end portion 2E having the suction port with the larger opening is forced to contact the inner volume control member 50, making the inner volume control member 50 move into the inner space 20A of the suction pump 20 as shown in FIG. 10. Accordingly, the inner volume of the inner space of the suction pump 20 is reduced, resulting in an increase of the pressure (negative pressure) of the suction pump. As a result, an optimum suction force can also be obtained in case of performing the suctioning operation through the use of the first end portion 2D having the suction port with the smaller opening.

While the invention has been shown and described with respect to the preferred embodiment, it will be understood by those skilled in the art that various changes and modification may be made without departing from the spirit and scope of the invention as defined in the following claims.

What is claimed is:

1. A skin care device comprising:
a suction pump for generating a suction force;
a suction nozzle detachably attached to a mounting portion of the suction pump and including a first end portion having a suction port with a smaller opening and a second end portion having a suction port with a larger opening, wherein both of the first end portion and the second end portion are capable of being attached to the mounting portion;
a sealing member disposed between an inner peripheral surface of the mounting portion and an outer peripheral surface of the suction nozzle, for sealing a gap between the mounting portion and the suction nozzle; and
an inner volume control member for changing the volume of an inner space of the suction pump depending on whether the first end portion or the second end portion of the suction nozzle is attached to the mounting portion,
wherein the inner volume control member is selectively moved by one of the end portions of the suction nozzle to change the volume of the inner space of the suction pump.

2. The device of claim 1, wherein the sealing member is provided at an inner peripheral portion of the mounting portion.

3. The device of claim 1, wherein the sealing member is provided at an outer peripheral portion of the suction nozzle.

4. The device of claim 1, wherein the opening of each suction port has an approximately circular or elliptical shape.

5. The device of claim 1, wherein the suction nozzle is formed of a resilient material.

6. The device of claim 1, further comprising:
a mist nozzle installed in the vicinity of the suction nozzle, for spraying a mist of a liquid;
a tank for storing therein the liquid to be supplied into the mist nozzle; and
a liquid supply pump for supplying the liquid in the tank into the mist nozzle,
wherein the opening of each suction port is of an approximately elliptical shape and the suction nozzle is attached to the mounting portion of the suction pump such that the a direction of a longer diameter of the elliptical opening of each suction port faces toward the mist nozzle.

7. The device of claim 1, wherein one or more holes for passing an exterior air therethrough are provided at the inner peripheral surface of the mounting portion to reduce the suction force while suctioning skin impurities by bring the mounting portion in direct contact with a skin.

8. The device of claim 1, further comprising an anti-slipping member for preventing the suction nozzle from slipping when the suction nozzle is connected to or separated from the mounting portion, wherein an anti-slipping member is provided at the outer peripheral portion of the suction nozzle.

9. The device of claim 1, the volume control member is slidably movable in the inner space of the suction pump.

10. The device of claim 1, wherein one of the end portions of the suction nozzle is a suctioning passage directly contacting to a user's skin, when the other end portion of the suction nozzle is attached to the mounting portion.

11. The device of claim 1, wherein both of the end portions of the suction nozzle are selectively attached directly to the mounting portion.

12. The device of claim 1, wherein, in case the second end portion of the suction nozzle is attached to the mounting portion of the suction pump, the second end portion is forced to contact the inner volume control member, making the inner volume control member move into the inner space of the suction pump and reducing the volume of the inner space of the suction pump, and
wherein, in case the first end portion of the suction nozzle is attached to the mounting portion of the suction pump, the first end portion dose not contact the inner volume control member, not making the inner volume control member move into the inner space of the suction pump and not reducing the volume of the inner space of the suction pump.

13. The device of claim 9, wherein, in case the second end portion of the suction nozzle is attached to the mounting portion of the suction pump, the second end portion is forced to contact the inner volume control member, making the inner volume control member move into the inner space of the suction pump and reducing the volume of the inner space of the suction pump, and
wherein, in case the first end portion of the suction nozzle is attached to the mounting portion of the suction pump, the first end portion dose not contact the inner volume control member, not making the inner volume control member move into the inner space of the suction pump and not reducing the volume of the inner space of the suction pump.

\* \* \* \* \*